(12) United States Patent
Piskun

(10) Patent No.: US 7,118,528 B1
(45) Date of Patent: Oct. 10, 2006

(54) HEMORRHOIDS TREATMENT METHOD AND ASSOCIATED INSTRUMENT ASSEMBLY INCLUDING ANOSCOPE AND COFUNCTIONING TISSUE OCCLUSION DEVICE

(76) Inventor: Gregory Piskun, 113 Laredo Dr., Morganville, NJ (US) 07751

( * ) Notice: Subject to any disclaimer, the term of this patent is extended or adjusted under 35 U.S.C. 154(b) by 8 days.

(21) Appl. No.: 10/801,283

(22) Filed: Mar. 16, 2004

(51) Int. Cl.
*A61B 1/00* (2006.01)

(52) U.S. Cl. .................. 600/105; 606/110; 606/111; 606/112; 606/113; 606/197; 606/205; 606/206; 606/157; 606/158; 606/219; 606/142; 600/129; 227/175.2; 227/175.1; 227/19; 227/180.1

(58) Field of Classification Search .................. 606/51, 606/52, 110, 205–207; 600/105, 129; 227/175.2, 227/19
See application file for complete search history.

(56) References Cited

U.S. PATENT DOCUMENTS

| 457,787 | A | * | 8/1891 | Leisenring | .................. 600/184 |
| 5,655,698 | A | | 8/1997 | Yoon | |
| 6,142,933 | A | | 11/2000 | Longo et al. | |
| 6,343,731 | B1 | * | 2/2002 | Adams et al. | ............ 227/180.1 |
| 6,428,473 | B1 | * | 8/2002 | Leonard et al. | ............. 600/219 |
| 6,494,881 | B1 | * | 12/2002 | Bales et al. | .................... 606/45 |
| 6,616,603 | B1 | | 9/2003 | Fontana | |
| 6,923,806 | B1 | * | 8/2005 | Hooven et al. | ................ 606/41 |

\* cited by examiner

*Primary Examiner*—Linda C. M. Dvorak
*Assistant Examiner*—Matthew J. Kasztejna
(74) *Attorney, Agent, or Firm*—R. Neil Sudol; Henry D. Coleman; William J. Sapone

(57) ABSTRACT

A surgical instrument assembly for the treatment of hemorrhoids includes an anoscope and a hemorrhoid occlusion device. The anoscope includes a hollow body closed at a distal end and at least partially open at a proximal end to define a longitudinal channel. The hollow body has a sidewall provided with a window spaced from the distal end and the proximal end. A shutter member is slidably attached to the hollow body for selectively covering the window during an insertion operation and for opening the window to allow hemorrhoidal tissues to protrude through the window into the anoscope. The hemorrhoid occlusion device includes an instrument shaft provided at a distal end with two jaws, at least one of the jaws including a C- or U-shaped clamping member movable alternately away and towards the other of the jaws for clamping and occluding hemorrhoidal tissues protruding through the window into the anoscope.

31 Claims, 6 Drawing Sheets

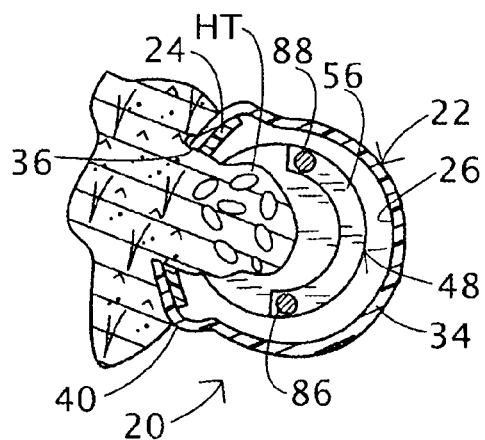
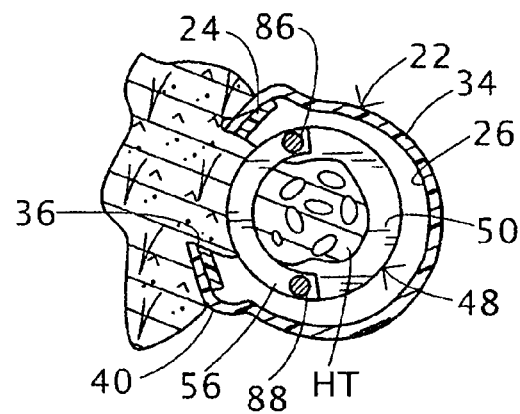
FIG. 8      FIG. 9
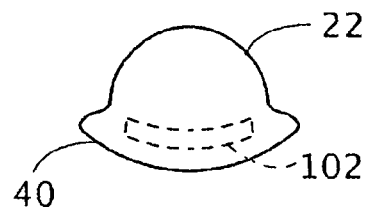
FIG. 10
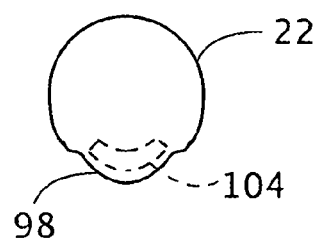
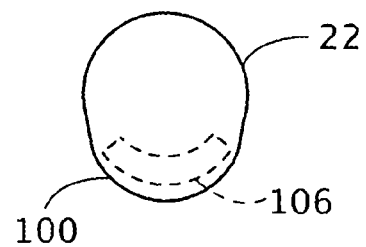
FIG. 11      FIG. 12

HEMORRHOIDS TREATMENT METHOD AND ASSOCIATED INSTRUMENT ASSEMBLY INCLUDING ANOSCOPE AND COFUNCTIONING TISSUE OCCLUSION DEVICE

FIELD OF THE INVENTION

This invention relates to the treatment of hemorrhoids and more specifically to a hemorrhoid treatment method wherein the base of a hemorrhoid is compressed by jaws of a clamping instrument, and then the vascular supply of the hemorrhoid is occluded by application of an impact or energy. This invention also relates to an assembly including a hemorrhoidal clamp and an anal port designed to accomplish this task.

BACKGROUND OF THE INVENTION

Hemorrhoidal disease is a very common condition, affecting more than half of people at age 50. Approximately 500,000 patients receive one or another type of interventional treatment annually in the United States for symptomatic hemorrhoids. Approximately 160,000 patients a year in the U.S. undergo surgical excision of hemorrhoids.

The term "hemorrhoid" is generally used to refer to the disturbing perianal symptoms related to vascular complexes in the lower rectum and anus. This is usually associated with enlargement of this naturally occurring vascular tissue, which is responsible for its subsequent bleeding, prolapsing, thrombosis, itching, burning, etcetera. The word "hemorrhoids" originates from Greek "haimorrhoos" (haimo—hemo+rhein—to flow), which means "flowing with blood." The word "pile" is a synonym for hemorrhoid, which originates from Latin "pila"—"ball."

Repetitive straining due to constipation appears to be a leading factor in forming and progressing of hemorrhoids. The chances of having symptomatic hemorrhoids increase with age, pregnancy, obesity, sedimentary life, heavy lifting and genetic predisposition.

The rectum is arbitrarily separated from the anus by the so-called dentate line. Rectal mucosa is free of pain receptors. The procedures limited to the rectal mucosa, therefore, generally are not associated with pain. In contrast, anal mucosa contains many pain receptors and is, therefore, very sensitive to painful stimuli. Hemorrhoids, located in the rectum, are called internal. Internal hemorrhoids are located within the submucosal layer. External hemorrhoids are located in the anus. Internal and external hemorrhoids have generally different clinical presentation and complications. Internal hemorrhoids are prone to bleeding and prolapsing outside of the anal ring. A prolapsed internal hemorrhoid can easily become traumatized and strangulated by a spastic anal sphincter. External hemorrhoids may rupture, causing painful subcutaneous lumps in the perianal area, which is frequently referred to as "thrombosed external hemorrhoids". Thrombosis of external hemorrhoid may lead to ulceration of the overlying tissues and bleeding. Both types of hemorrhoids may be responsible for perianal discomfort, itching, irritation, impeding of perianal hygiene, loss of work time and measurable decrease of quality of life.

Treatment is tailored to the type and severity of hemorrhoids. Pharmacological treatment, which is aimed at the regulation of defecation and symptomatic relief, is notorious for having only temporary and frequently incomplete effect. Current interventional, non-excisional, therapies are designed to obliterate blood supply to part of or to the entire hemorrhoid (rubber band ligation, infrared coagulation, injection sclerotherapy, ultrasound guided hemorrhoidal artery ligation). These have modest, inconsistent clinical success with frequent recurrences.

Rubber band ligation is the most popular method of treatment of hemorrhoids in the United States. The technique was described by Blaisdell in 1963. It is quick and not expensive. In this procedure, some hemorrhoidal tissue is pulled into the ligator and a rubber band is placed around the base of the pulled tissue. This causes essentially a strangulation of the blood supply to a portion of the internal hemorrhoid and its overlying rectal mucosa. An ischemic necrosis and autoamputation of the hemorrhoid follows in a few days, leaving an open rectal wound, which heals over several days. Significant postprocedural pain, affecting daily routine, is rare and is probably related to the placement of the band too close to the dentate line (pain-sensitive area). Although rubber band ligation is very effective for immediate bleeding control of small internal hemorrhoids, frequently several treatments of a single larger hemorrhoid are required in order to achieve substantial size reduction. Since the significant portion of the hemorrhoid is usually not removed, recurrences are frequent. In addition, since this treatment leaves the patient with an open wound in the anus for several days or weeks, rubber band ligation might be rendered unsuitable for HIV-positive patients and requires demanding preparation for patients with inherited, acquired and iatrogenic coagulopathy.

Sclerotherapy is another method to treat first- and second-degree internal hemorrhoids. The delivery of a sclerosing agent is accomplished through a single fine needle, attached to the syringe, and is intended to be within the vascular lumen. Since a hemorrhoid is essentially a ball of multiple twisted vascular lumens, it is virtually impossible to deliver sclerosing agent with the desired precision. The rates of complications and recurrence are high.

Ultrasound guided hemorrhoidal artery ligation involves manual suturing of the rectal tissues containing the hemorrhoial artery. The artery is located by the ultrasound. A resulting regression of the corresponding internal hemorrhoid is expected. Since suture-ligation is performed above the internal hemorrhoid in the pain-insensitive zone, the procedure should be painless. The technique is demanding and is highly dependent on the operator's experience and dexterity. Inexperience or lack of skill is responsible for both "missing" the hemorrhoidal artery and inadvertent rectal and vascular injuries. Hemorrhoidal artery injuries with resulting severe bleeding, rectal wall injury, etc. have been reported. Recurrences are frequent.

Infrared coagulation of a hemorrhoidal artery involves delivery of the infrared coagulation energy to the hemorrhoidal artery and causes subsequent regression of the corresponding internal hemorrhoid. Since the exact location of the artery is not known and is only presumed to be just proximal to the internal hemorrhoid, several blind infrared firings are required to improve the chance of reaching the hidden target. Several sessions of treatments in a time span of several weeks is recommended. The proper application of the infrared probe is more difficult with larger hemorrhoids due to obscurity of the interface between the probe and mucosa. Recurrences are frequent.

None of the above described techniques adequately addresses tissue redundancy and tissue prolapse, which frequently accompany more advanced stages (late $2^{nd}$, $3^{rd}$ and $4^{th}$) of hemorrhoidal disease and, therefore, can be considered only for the treatment of $1^{st}$ and early $2^{nd}$ stages of internal hemorrhoids. Even then, the rate of recurrence is substantial, reflecting the deficiencies of the existing methods.

The only approach which has been found to be consistently effective in the long-lasting control of the hemorrhoidal symptoms is the surgical excision of the hemorrhoids. There are two main methods of surgical excision of internal hemorrhoids: traditional surgical excision (longitudinal hemorrhoidectomy) and the so-called Procedure for Prolapse and Hemorrhoids or PPH (transverse hemorrhoidectomy with circular stapler).

Traditional surgical excision of hemorrhoids is a very effective but debilitating form of treatment. The hemorrhoidal tissue essentially is removed in longitudinal fashion down to the underlying internal sphincter. Traditional surgical excision almost invariably extends the anal trauma to and beyond the dentate line, thus causing severe postoperative pain. The technique is highly dependent on the technical skill of the operator. Surgical excision of hemorrhoids requires anesthesia and causes severe perianal pain for several weeks and significant loss of work time.

The so-called Procedure for Prolapse and Hemorrhoids (PPH) involves circumferential excision of the prolapsed rectal mucosa and submucosal layer with a circular stapler. Since excision is done in the pain insensitive area (above the dentate line), a decreased postoperative pain and faster recovery when compared to traditional hemorrhoidectomy are observed. The internal hemorrhoids purportedly shrink within four to six weeks after the procedure. Advocates of PPH claim less pain and faster recovery, but the technique requires anesthesia and a demanding technical and instrumental set-up. In addition, this technique creates substantial circumferential rectal trauma, which is clearly excessive in the majority of cases when only 1 or 2 hemorrhoids are enlarged. Serious complications have been reported. A substantial circumferential injury of the anal canal and subsequent scarring may cause anal stricture (narrowing), which is debilitating and difficult to treat. The technique requires massive anal dilation in order to accommodate a large head assembly of the circular stapler, which by itself presents an additional source of postoperative anal discomfort and potential anal trauma (anal fissures, bleeding, etc.). The main achievement of PPH technique over traditional hemorrhoidectomy is the placement of the surgical injury line in transverse fashion above the dentate line.

In summary, although many minimally invasive techniques have been introduced to treat symptomatic internal hemorrhoids, these entail a high rate of recurrence and a need for repetitive procedures. Approximately 15–20% of patients undergoing an intervention for treatment of their internal hemorrhoids require surgical excision of hemorrhoids, mainly because the current non-excisional techniques do not address or address inadequately (rubber band ligation) the accompanying anal mucosal prolapse and tissue redundancy. Some groups of patients, such as HIV-positive patients, and patients with spinal cord injuries, coagulopathy, etc, have absolute or relative contraindications to the existing techniques. The Procedure for Prolapse and Hemorrhoids addresses many of the deficiencies of the existing techniques, but involves a demanding technical and instrumental set-up, requires general or regional anesthesia, and is designed to perform frequently unnecessary circumferential rectal injury.

There is a need, therefore, for a device which allows fast and effective treatment of hemorrhoids in minimally invasive (innocent tissues are spared) and painless fashion (excisional line is placed above the dentate line). In addition, an anal port, which would facilitate an application of such a device in the rectum, is also desirable.

OBJECTS OF THE INVENTION

It is an object of the present invention to provide an improved method for the surgical treatment of hemorrhoidal tissues.

It is a more specific object of the present invention to provide a surgical method that is less traumatic than prior art methods for the surgical treatment of hemorrhoids.

Another relatively specific object of the present invention is to provide a surgical method for the treatment of hemorrhoids, that may appropriately be carried out in an office, rather than requiring an operating room.

It is a related object of the present invention to provide an anoscope that may be used in carrying out the method of the invention.

Another related object of the present invention is to provide a tissue occlusion device that may be used in carrying out the method of the invention.

A further object of the present invention is to provide a surgical instrument assembly for treating one or more hemorrhoids with any severity of enlargement and prolapse.

These and other objects of the present invention will be apparent from the drawings and descriptions herein. Although every object of the invention is believed to be attained in at least one embodiment of the invention, there is not necessarily any single embodiment that attains all of the objects of the invention.

SUMMARY OF THE INVENTION

The present invention is directed in part to a device having a hemorrhoidal clamp, a source of energy to be delivered to clamped tissue, and an actuating mechanism for a focused delivery of such energy. The device has distally located C-curve clamp or C-curve jaws, a handle actuating the clamping action and the delivery of energy; an instrument connecting the clamp and the handle and carrying necessary components for transporting an obliterating impact to the base of the clamped hemorrhoid. The clamp is placed at the base of an internal hemorrhoid in the transverse direction in relation to the rectal axis above the dentate line. The operator then compresses the hemorrhoidal tissue and overlying anal mucosa. A vessel obliterating impact is subsequently delivered to the compressed base of the hemorrhoid from the energy source. The energy may be infrared radiation, electrical, chemical (sclerosing agents), mechanical (staples with and without distal transaction by knife), etcetera. The actuating mechanism is energy source specific, for effective and efficient delivery of energy to the compressed hemorrhoidal base. The present invention allows treatment of selected number of hemorrhoids in the pain-free zone with a preferred kind of energy. Most importantly, since the energy is delivered across the hemorrhoidal base between the jaws of the clamp, the tissue trauma is limited to the targeted area without potentially compromising the underlying innocent rectal tissues, hence minimizing operative trauma.

The present invention is also directed in part to an anal port or anoscope, which is adapted for an adequate anal maneuvering of the hemorrhoid treatment device. The anoscope is generally a hollow conical structure consisting of a channel body and a proximal sliding insert. The distal half of the cannula is substantially symmetrical about a longitudinal axis. The proximal portion of the instrument is assymetrical about its longitudinal axis as a result of an outward assymetrical wall protrusion. This protrusion carries a proximal slot, which is alternately opened and closed by the longitudinally sliding insert. When this slot is opened partially or completely, an operative window is created. The hemorrhoid of interest is allowed to protrude through the window into the lumen of the anal port. The protruding hemorrhoid is treated by the application of the hemorrhoidal clamp and the delivery of a vessel-obliterating impact at the clamped base of the hemorrhoid. The chosen type of energy (staples—mechanical; sclerosing agent—chemical and mechanical; infrared, laser, electrical, etc.) and energy characteristics are used to accomplish the obliteration of the vessels at the base of target hemorrhoid. When the window is opened, the present design facilitates the presentation of the treated internal hemorrhoid into the operative field, i.e., pushes the hemorrhoid into the anoscopes's lumen, while retracting away and protecting the surrounding innocent tissues. When the proximal window is closed the anal port effectively has a contiguously connected distal blind tip, an elongated channel body, and a flange. The flange is extended outwardly from the channel body.

Upon the insertion of the anal port, the target hemorrhoid is localized through the transparent anoscope's wall. The center of the outwardly concaved proximal wall is positioned over the hemorrhoid. The window is opened to the desired size by moving the sliding insert proximally, whereupon the hemorrhoid protrudes into the lumen of the anoscope through the window. If needed, the hemorrhoid is gently pulled with an atraumatic forceps further into the lumen. The hemorrhoid device is inserted in the lumen of the anal port under the direct view of the operator. The hemorrhoid is clamped at the base. The C-shape of the clamp allows it to be accommodated in the cylindrical anal cannula due. Congruency of the clamp and the anoscope protrusion allows one to more effectively reach the base of the hemorrhoid and minimize the trauma to the collateral rectal tissues. The obliterating impact to the hemorrhoidal vessels is initiated at the device handle. Again, the energy that is used to obliterate the target hemorrhoidal vessels at their base can be mechanical (staples), infrared, laser, electrical, etc. A sclerosing agent delivered to the vessels at their base will cause the sclerosing reaction, and hence, obliterating effect. In case of mechanical obliteration of the vessels by mean of the closed staples, due to its immediate and full effect, the hemorrhoid, located distally to the staple line, can be excised with knife, which is incorporated in the stapling device. The blind tip of the anal port allows the isolation of the operative field from the rest of colon, hence preventing the field from contamination. This also eliminates the need for preoperative rectal preparation.

An anoscope for hemorrhoidal surgery comprises, in accordance with the present invention, a hollow body and a shutter member. The hollow body defines a longitudinal channel which is closed at a distal end and at least partially opened at a proximal end. The opening at the proximal end is provided for enabling visualization of a surgical site and for the insertion of instrumentation. The hollow body has a sidewall provided with a window spaced from at least the distal end. The shutter member is movably mounted to the hollow body to cover the window during a positioning of the anoscope in an anal canal. The shutter member is removable from the window to permit hemorrhoidal tissues to protrude through the window into the channel. The open window has dimensions that are sufficiently large as to enable the protrusion of a hemorrhoid into the channel of the anoscope through the window.

Pursuant to preferred features of the present invention, the shutter member is slidably mounted to the hollow body, is disposed in the hollow body, and has a shape conforming to the sidewall in a region thereof about the window. The shutter member may be located in a track in the hollow body. The track may take the form of a shallow depression or recess with edges serving as guides for the sliding shutter member.

The hollow body generally has a longitudinal axis, and the sidewall is formed with a bulging portion located on one side of the axis and extending from the proximal end of the hollow anoscope body partially along a length of the sidewall towards the distal end. The window is located in the bulging portion, and the shutter member is slidable along and in engagement with the bulging portion. The window may generally take any shape suitable for the admission of protruding hemorrhoidal tissues. Rectangular and circular are possible shapes.

The hollow body of the anoscope has a rim surrounding the opening at the proximal end. The hollow body is preferably provided along the rim with a flange serving as a stop for preventing the anoscope from slipping entirely into the anal canal. The hollow body is further provided along the rim with a cutout disposed on a side of the axis opposite the bulging portion. The cutout facilitates manipulation of any instrument that is inserted into the anoscope for operating on hemorrhoidal tissues. In addition, the cutout facilitates visualization of the window and of hemorrhoidal tissues protruding into the longitudinal channel through the window. In other words, the cutout prevents obstruction to stapler/clamp manipulations and to the view of the opposite section. This design enables a wider range of motion of the stapler/clamp and better angle views during application of the stapler/clamp.

The anoscope is advantageously provided as part of a surgical instrument assembly that also includes a hemorrhoid treatment device comprising an instrument shaft, a handle (actuator) connected to the shaft at a proximal end thereof, and a pair of jaws mounted to the shaft at a distal end thereof. The handle is operatively connected to the jaws for alternatively opening and closing the jaws. At least one of the jaws takes the form of a C- or U-shaped clamping member movable alternately away and towards the other jaw. Preferably, each of the jaws takes the form of a C- or U-shaped clamping member movable alternately away and towards the other jaw. A hemorrhoid occlusion component is mounted to the jaws for acting on tissues gripped between the jaws, to couple the tissues to each other.

In accordance with a preferred feature of the present invention, at least the proximal jaw has a U or C shape while the distal end portion of the instrument shaft has a U- or C-shaped cross-section that is aligned with the proximal jaw to provide a line of sight along the instrument and into the anoscope after insertion of the distal end of the hemorrhoid treatment device into the anoscope.

The hemorrhoid occlusion component may take any form capable of bonding organic tissues, particularly hemorrhoidal tissues, to one another. Thus, the hemorrhoid occlusion component may be a stapling mechanism or an injection mechanism connectable to a reservoir of a sclerosing composition. In the case of an injection mechanism, one or both of the jaws may be provided with one or more hollow needles for distributing the sclerosing composition from the reservoir into the hemorrhoids. Alternatively, the hemorrhoid occlusion component may include an applicator of radiant energy, for instance, in the infrared or optical portions of the electromagnetic spectrum. For example, the hemorrhoid occlusion component may include optical fibers connectable to a source of laser radiation.

Pursuant to additional features of the present invention, at least the distal jaw is mounted to a pair of parallel rods each connected at one end to the instrument shaft, the jaws being connected to one another and to the instrument shaft (e.g., via the parallel rods) so that the jaws remain parallel to one another (e.g., perpendicular to the rods) during opening and closing strokes.

Pursuant to more particular features of the present invention, one of the jaws (e.g., the distal jaw) is slidably coupled to the rods, while the other jaw (e.g., the proximal jaw) is fixed with respect to the rods, and the rods are coupled to the distal jaw on opposite sides thereof.

The jaws and rods may be manufactured as a disposable cartridge assembly, optionally detachable from the instrument shaft.

A method for the treatment of hemorrhoids, in accordance with the present invention, utilizes an anoscope and a hemorrhoid occlusion device. As discussed above, the anoscope preferably includes a hollow body having a sidewall provided with a window, while the hemorrhoid occlusion device has a distal end provided with a pair of jaws, at least one of the jaws including a C- or U-shaped clamping member. The method includes (i) inserting the anoscope into an anal canal, (ii) manipulating the anoscope so that hemorrhoidal tissues protrude through the window into the anoscope, (iii) inserting the jaws of the occlusion device into the anoscope, (iv) manipulating the occlusion device, after the protruding of the hemorrhoidal tissues through the window and after the inserting of the jaws into the anoscope, so that the jaws are located on opposite sides of the hemorrhoidal tissues, (v) thereafter closing the jaws to clamp the hemorrhoidal tissues, and (vi) subsequently operating a tissue occlusion component of the occlusion device to permanently constrict a portion of the hemorrhoidal tissues.

The window is preferably spaced from a distal end of the anoscope sidewall. The window may additionally be spaced from a proximal end of the anoscope sidewall. The spacing of the window particularly from the proximal end of the anoscope is equal to the expected distance of hemorrhoids from the anal orifice.

The manipulating of the anoscope generally includes turning the anoscope about a longitudinal axis so that the hemorrhoidal tissues are aligned with the window. Thus, the hemorrhoidal tissues are able to protrude through the window into the anoscope. Typically, the turning of the anoscope is carried out before the insertion of the occlusion device into the anoscope. Otherwise, the occlusion device is liable to obstruct a proper visualization of the hemorrhoidal tissues for purposes of, inter alia, aligning the tissues with the window.

Where the distal jaw of the occlusion device is formed as a C- or U-shaped clamping member, a slot or gap in the jaws facilitates a sliding of the distal end of the occlusion device into the anoscope while the hemorrhoidal tissues are protruding into the anoscope. Prior to an insertion stroke of the occlusion device into the anoscope, the device is rotated about a longitudinal axis so that the slot or gap in the distal jaw is aligned with the protruding hemorrhoidal tissues. In this way, the distal jaw can be inserted past the protruding hemorrhoidal tissues to lie on an inward side of those tissues. Subsequently, the occlusion device is rotated so that the hemorrhoidal tissues are positioned in between the jaws of the occluding device. The jaws can then be closed and the occlusion process completed.

The above-described rotation procedure may be dispensed with where the occlusion device is permitted to wiggle within the anoscope past and over the protruding hemorrhoid. In this deployment procedure, the occlusion device may be inserted with convex outer surfaces of the jaws facing towards the window in the anoscope, so that no rotation is necessary. The hemorrhoidal tissues are generally sufficiently pliable so as to deform and slip past the occlusion jaws during an insertion and deployment operation.

The anoscope may be made of a transparent polymeric material that facilitates visual inspection and locating of the hemorrhoids. The jaws of the occlusion device are inserted into the anoscope after the inserting of the anoscope into the anal canal, after the manipulating of the anoscope to align the window with hemorrhoidal tissues, and after the protruding of the hemorrhoidal tissues through the window.

Where the anoscope includes a shutter member for covering the window, the inserting of the anoscope into the anal canal includes inserting the anoscope with the shutter member covering the window. The method then further comprises moving the shutter member to uncover the window to permit the hemorrhoidal tissues to protrude through the window. The moving of the shutter member preferably includes sliding the shutter member relative to the anoscope, for instance, in a longitudinal and proximal direction out of the anoscope.

As discussed above, the sidewall of the anoscope may be formed with a bulging portion located on one side of the anoscope axis and extending from a proximal end of the anoscope partially along a length of the sidewall towards a distal end of the anoscope, the window being located in the bulging portion. In that case, the shutter member is slid along and in engagement with the bulging portion pf the anoscope.

The bulging portion of the anoscope serves as a retractor of collateral anal/rectal tissues. In addition, the protrusion creates more workspace in the area of hemorrhoid. This design allows for better access to the base of the hemorrhoid, which is located in the submucosal layer close to the rectal muscle.

As further discussed above, the hemorrhoid occlusion component may take any form capable of bonding organic tissues, particularly hemorrhoidal tissues, to one another. Thus, the hemorrhoid occlusion component may be a stapling mechanism or an injection mechanism connectable to a reservoir of a sclerosing composition. In the case of an injection mechanism, one or both of the jaws may be provided with one or more hollow needles for distributing the sclerosing composition from the reservoir into the hemorrhoids. Alternatively, the hemorrhoid occlusion component may include an applicator of radiant energy, for instance, in the infrared or optical portions of the electromagnetic spectrum. In that event, the hemorrhoid occlusion component may include optical fibers connectable to a source of laser radiation.

Accordingly, the operating of the tissue occlusion component may include stapling the hemorrhoidal tissues, injecting the hemorrhoidal tissues with a sclerosing composition, or irradiating the hemorrhoidal tissues.

Preferably, the jaws are maintained in parallel to one another during their closing.

A surgical instrument assembly for the treatment of hemorrhoids comprises, in accordance with the present invention, an anoscope and a hemorrhoid occlusion device, where the anoscope includes a hollow body closed at a distal end and at least partially open at a proximal end to define a longitudinal channel. The hollow body has a sidewall provided with a window spaced from at least the distal end. The hemorrhoid occlusion device includes an instrument shaft provided at a distal end with two jaws, at least one of the jaws including a C- or U-shaped clamping member movable alternately away and towards the other of the jaws for clamping and occluding hemorrhoidal tissues protruding through the window into the anoscope.

The present invention offers to provide minimally invasive treatment of one or more hemorrhoids through an anal cannula having a normal size or any degree of enlargement and protrusion. The approach of the present invention recommends the application of a staple line in a transverse direction (in relation to the anal axis) above the so-called dentate line (the dentate line is an anatomical line in the anal canal, above which the mucosa is pain-insensitive). Since the C-curve of the tissue-occluding jaws in a closure device of the present invention is essentially a circular section, all the advantages of circular stapling can be attained in the present methodology without the disadvantages. A smaller stapling cartridge or jaws with a different C-curve (more or less curved) can be used for smaller hemorrhoids or different rectums as needed without the potential of rectal narrowing or substantial collateral ano-rectal trauma, which accompany the method of U.S. Pat. No. 6,142,933. The particular anal port or anoscope design of the present invention, together with the C-curved stapler clamp, allows treatment of the chosen number of hemorrhoids without incurring unnecessary surgical trauma and expense. The anoscope and tissue-occluding device of the present invention can be used in the office without the need for trained medical assistance. Less surgical trauma, particularly in the treatment of hemorrhoids, translates into a reduced loss of work and interruption of normal life.

BRIEF DESCRIPTION OF THE DRAWINGS

FIG. 8 is a schematic transverse cross-sectional view taken along line IX—IX in FIG. 7D.

FIG. 9 is a schematic transverse cross-sectional view taken along line VIII—VIII in FIG. 7C.

FIG. 10 is a diagrammatic transverse cross-section of the anoscope of FIGS. 1 and 7A–7F.

FIG. 11 is a diagrammatic transverse cross-section similar to FIG. 10, showing an alternative design of the anoscope of FIGS. 1 and 7A–7F.

FIG. 12 is a diagrammatic transverse cross-section similar to FIG. 10, showing another alternative design of the anoscope of FIGS. 1 and 7A–7F.

DETAILED DESCRIPTION OF THE PREFERRED EMBODIMENTS

Figure 1:
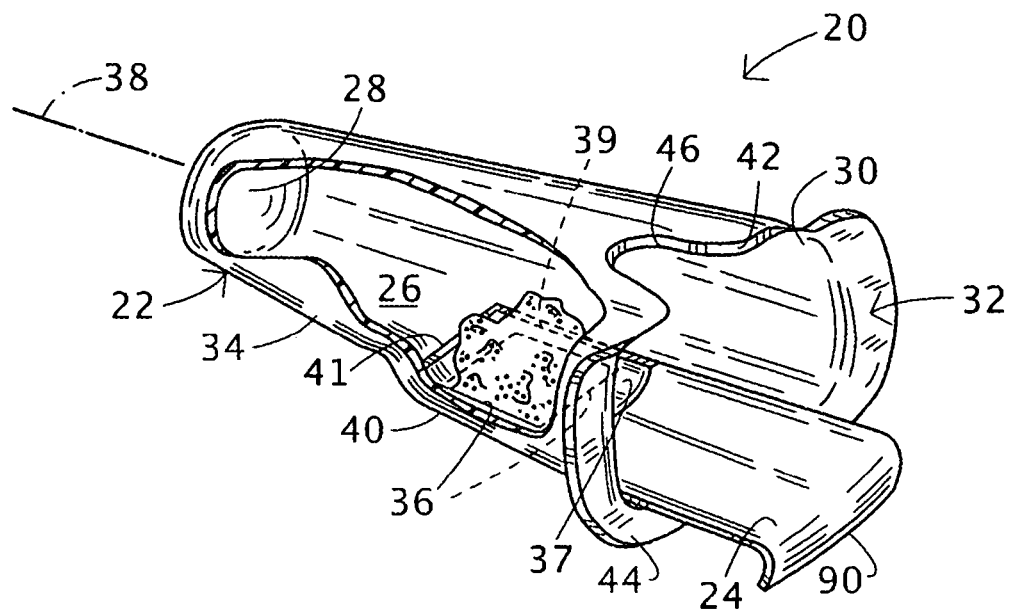
FIG. 1 is a schematic perspective view, partially broken away, of an anoscope in accordance with the present invention, for use in a method in accordance with the present invention, showing a pair of jaws.

As illustrated in FIG. 1, an anoscope 20 for hemorrhoidal surgery comprises a hollow body 22 and a shutter member 24. Hollow body 22 defines a longitudinal channel or lumen 26 that is closed at a distal end 28 and formed with an opening 30 at a proximal end 32. Opening 30 enables visual inspection of a surgical site and the insertion of instrumentation. Hollow body 22 has a sidewall 34 provided with a rectangular window 36 spaced from distal end 28 and preferably also from proximal end 28 of hollow body 22.

Shutter member 24 is movably mounted to hollow body 22 to cover window 36 during a positioning of anoscope 20 in an anal canal. Shutter member 24 is removable from window 36 to permit hemorrhoidal tissues to protrude through window 36 into anoscope channel 26. More specifically, shutter member 24 is slidably mounted to hollow body 22, is disposed in hollow body 22, and has a shape conforming to sidewall 34 in a region thereof about window 36.

Shutter member 24 is located in a track 37 in the hollow body. Track 37 takes the form of a shallow depression or recess with longitudinal edges or shoulders 39 serving as guides for the sliding shutter member 24. A transverse edge or shoulder 41 serves as an abutment to continued distal motion of shutter member 24 during an insertion stroke thereof. Shutter member 24 may be locked into track 37, for example, by grooves (not illustrated) in longitudinal edges or shoulders 39.

Hollow body 22 generally has a longitudinal axis 38, and sidewall 34 is formed with a bulging portion or protrusion 40 located on one side of the axis and extending from proximal end 32 of the hollow anoscope body partially along a length of sidewall 34 towards distal end 28. Window 36 is located in bulging portion 40, and shutter member 24 is slidable along and in engagement with bulging portion 40. As shown in FIGS. 8, and 9, shutter member 24 and bulging portion 40 may be cooperatively formed so that the bulging portion serves as a track that slidably retains the shutter member. Window 36 may generally take any shape suitable for the admission of protruding hemorrhoidal tissues HT (FIGS. 7B–7F, 8, and 9). Rectangular and circular are possible shapes.

Hollow body 22 of anoscope 20 has a rim 42 surrounding opening 30 at proximal end 32. Hollow body 22 is preferably provided along rim 42 with a flange 44 serving as a stop for preventing anoscope 20 from slipping entirely into the anal canal. Hollow body 22 is further provided along rim 42 with a cutout 46 disposed on a side of axis 38 opposite bulging portion 40. Cutout 46 facilitates manipulation of any instrument that is inserted into anoscope 20 for operating on hemorrhoidal tissues. In addition, cutout 46 facilitates observation of window 36 and of hemorrhoidal tissues HT protruding into longitudinal channel 26 through window 36.

In some applications, window 36 may extend in a proximal direction all the way to flange 44. In any case, window 36 is large enough for the admission of hemorrhoids into channel or lumen 26 of anoscope 20. The placement of window 36 in bulging portion or protrusion 40 is conducive to providing window 36 with properly large dimensions.

Figure 2:
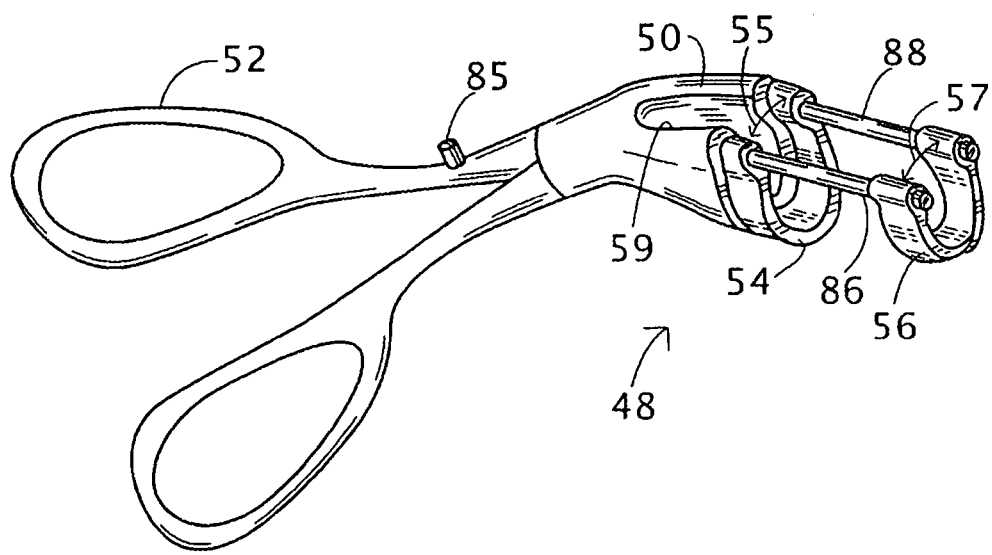
FIG. 2 is a schematic perspective view, partially broken away, of a tissue occlusion device in accordance with the present invention, for use in a method in accordance with the present invention.

Anoscope 20 may be provided as part of a surgical instrument assembly than also includes a hemorrhoid treatment device 48 depicted in FIG. 2. Device 48 comprises an instrument shaft 50, a handle or actuator 52 connected to the shaft at a proximal end thereof, and a pair of jaws 54 and 56 (proximal and distal) mounted to the shaft at a distal end thereof. Handle 52 is operatively connected to jaws 54 and 56 for alternatively opening and closing the jaws. Jaws 54 and 56 each takes the form of a C- or U-shaped clamping member movable alternately away from and towards the other jaw. Jaws 54 and 56 are insertable into anoscope 20 so that distal jaw 56 is located on a far or distal side of hemorrhoidal tissues protruding through window 36 into the anoscope, between the protruding hemorrhoidal tissues and an inner or distal end of the anoscope and so that jaw 54 is located on a near or proximal side of the protruding hemorrhoidal tissues, between the protruding hemorrhoidal tissues and an outer or proximal end of anoscope 20. Jaws 54 and 56 are mounted for linear translation alternately towards and away from one another. Jaws 54 and 56 define a C- or U-shaped occlusion area.

Jaws 54 and 56 define respective gaps 55 and 57. A distal end portion of instrument shaft 50 is U- or C-shaped in cross-section and defines a recess 59 aligned and communicating with gap 55. This asymmetrical shape of the distal end of instrument shaft 50 facilitates a visualization of a surgical site while a distal end portion of hemorrhoid treatment device 48 is inserted into anoscope 20.

Figure 3:
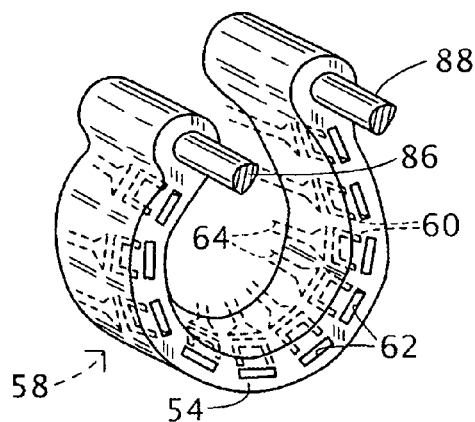
FIG. 3 is a schematic perspective view of a proximal one of the jaws depicted in FIG. 1, showing details of a tissue occlusion mechanism.

A hemorrhoid occlusion component is mounted to jaws 54 and 56 for acting on tissues gripped between the jaws, to couple the tissues to each other. The hemorrhoid occlusion component may take any form capable of bonding organic tissues, particularly hemorrhoidal tissues, to one another. As depicted in FIG. 3, the hemorrhoid occlusion component may take the form of a stapling mechanism 58 including a plurality of staples 60 disposed in an arcuate configuration inside proximal jaw 54. Staples 60 are longitudinally aligned on a distal side with respective ejection apertures 62 in jaw 54 and on a proximal side with respective pusher elements 64. Pusher elements 64 may be disposed on a proximal side in contact with a pressure application ring (not shown) or other force-transmission structure operatively connected at a proximal end with handle 52. Distal jaw 56 is provided with a series of anvil elements or areas (not shown) that are aligned with respective slots or ejection apertures 62, for causing staple closure upon firing.

Staples 60 may be housed in a disposable cartridge element that may be a portion or the entirely of proximal jaw 54. This variation permits a surgeon, proctologist or other medical practitioner to clamp plural hemorrhoids in the course of a single procedure. After the stapling of one hemorrhoid, as discussed below with reference to FIGS. 7A–7E, the empty cartridge (e.g., jaw 54) is removed and replaced with a similar loaded staple cartridge.

Figure 4:
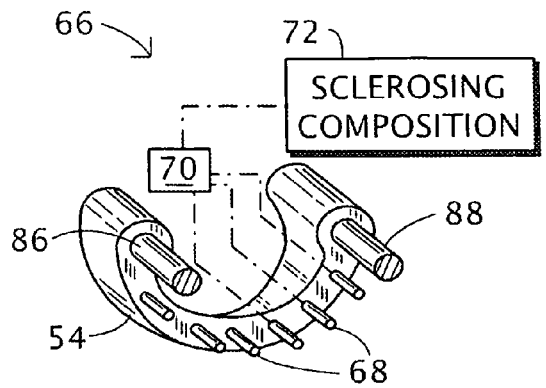
FIG. 4 is a schematic perspective view of the proximal jaw of FIG. 1, showing details of another tissue occlusion mechanism.

As illustrated in FIG. 4, an alternative hemorrhoid occlusion component takes the form of an injection mechanism 66 including a plurality of hollow needles 68 fixed to proximal jaw 54. Needles 68 are longitudinally oriented and circumferentially spaced about jaw 54. Needles 68 are connectable via a distribution manifold 70 to a reservoir 72 of a sclerosing composition such as a concentrated sugar solution or a biocompatible adhesive.

Figure 5:
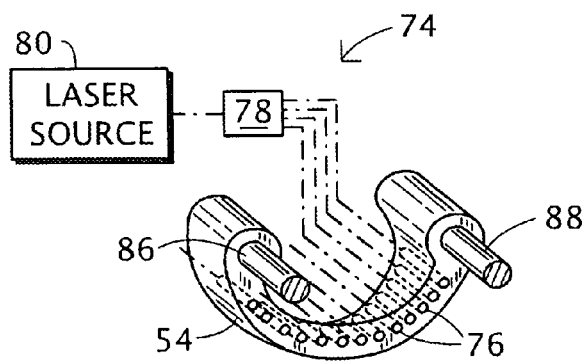
FIG. 5 is a schematic perspective view of the proximal jaw of FIG. 1, showing details of a further tissue occlusion mechanism.

FIG. 5 shows another alternative occlusion component in the form of a radiant-energy applicator 74, for instance, in the infrared or optical portions of the electromagnetic spectrum. More specifically, radiant-energy applicator 74 includes optical fibers 76 connectable via a distribution manifold 78 to a source 80 of laser radiation.

Figure 6:
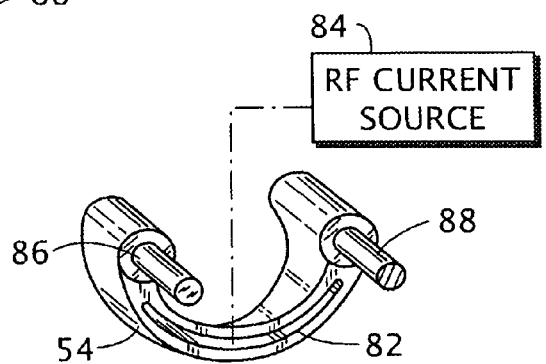
FIG. 6 is a schematic perspective view of the proximal jaw of FIG. 1, showing details of yet another tissue occlusion mechanism.

FIG. 6 depicts yet another alternative occlusion component in the form of an electrode 82 mounted to proximal jaw 54 and facing in the distal direction towards distal jaw 56. Distal jaw 56 may also be provided with an electrode (not shown), in the case of a bipolar delivery of electrical energy. Electrode 82 is connectable to a source 84 of radio-frequency current for delivering RF cauterizing current to hemorrhoidal tissues.

Jaws 54 and 56, together with rods 86 and 88, may form a disposable occlusion cartridge that is removable from shaft 50. Upon completion of a hemorrhoid treatment procedure on one patient, the cartridge is removed and replaced with a new cartridge for use on another patient.

In the case of injection mechanism 66, radiant-energy applicator 74, or electrode 82 electrode 82, handle 52 may be provided with a port or connector 85 for enabling the coupling of the hand-held hemorrhoid treatment device 48 to reservoir 72, laser source 80, or RF electric source 84, respectively.

As further illustrated in FIG. 2, jaws 54 and 56 are mounted to a pair of parallel rods 86 and 88 each connected at a proximal end to instrument shaft 50. Jaws 54 and 56 are connected to one another and to shaft 50 via rods 86 and 88 so that the jaws remain parallel to one another and perpendicular to rods 86 and 88 during opening and closing strokes of the jaws. Any reciprocatable drive mechanism known in the art or hereafter developed may be operatively coupled to jaws 54 and 56 and handle 52 for enabling opening and closing of jaws 54 and 56 by manipulation of handle 52.

In the embodiment of the hemorrhoid treatment device 48 shown in FIG. 2, distal jaw 56 is slidably coupled to rods 86 and 88, proximal jaw 54 is fixed with respect to the rods, and the rods are coupled to distal jaw 56 on opposite sides thereof. Jaws 54 and 56 and rods 86 and 88 may be manufactured as a disposable cartridge assembly detachable from instrument shaft 50. Alternatively, the operative components, such as staples 60 and apertures 62, may be formed as parts of a disposable cartridge separate from the jaws 54 and 56.

Figure 7A:
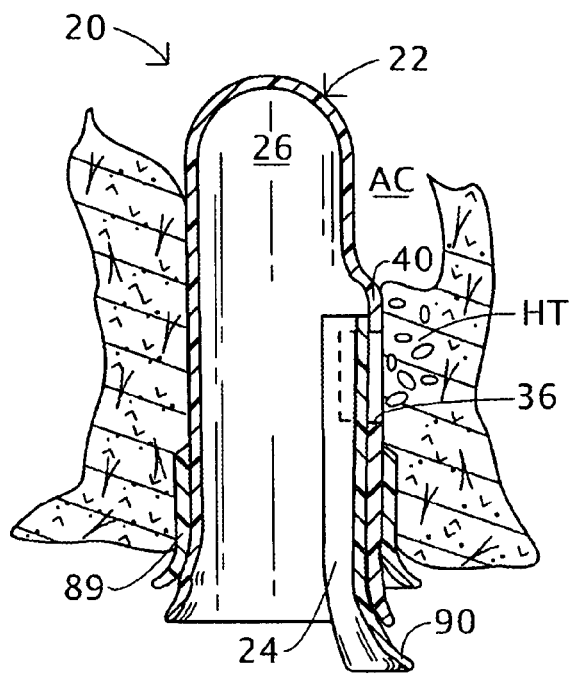
FIGS. 7A–7F are schematic cross-sectional views of the anoscope of FIG. 1 inserted into an anal canal, showing successive steps of a method in accordance with the present invention.

FIGS. 7A–7F illustrate steps in a method for the treatment of hemorrhoids utilizing anoscope 20 and hemorrhoid treatment device 48. As shown in FIG. 7A, anoscope 20 with shutter member 24 closing window 36 is inserted through a transparent anal port member 89 into an anal canal AC and is manipulated so that hemorrhoidal tissues HT are disposed adjacent to window 36. This procedure may involve longitudinally shifting and/or rotating the anoscope 20 inside the anal canal AC until the anoscope is in the desired position relative to the hemorrhoidal tissues HT. To that end, shutter member 24 and optionally sidewall 34 of hollow body 22 are made of a transparent polymeric material. Thus, anal tissues can be visualized through sidewall 34 and shutter member 24 during the manipulation of anoscope.

Figure 7B:
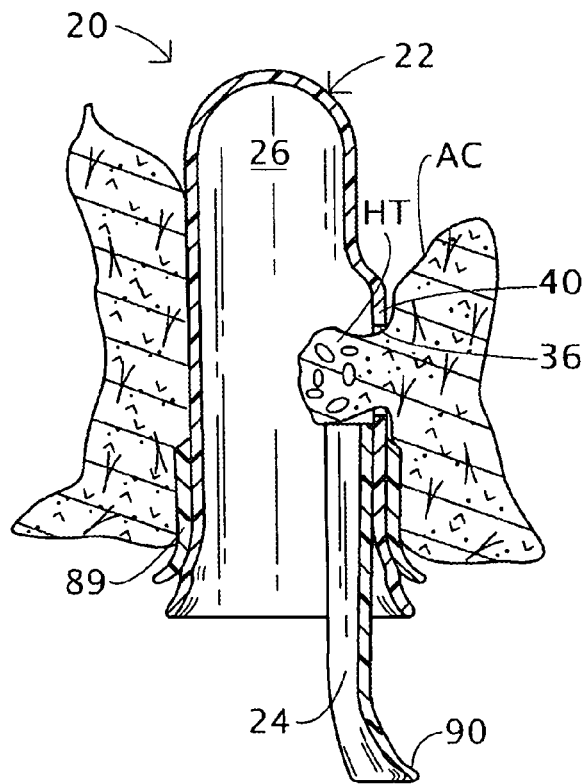
Figure 7C:
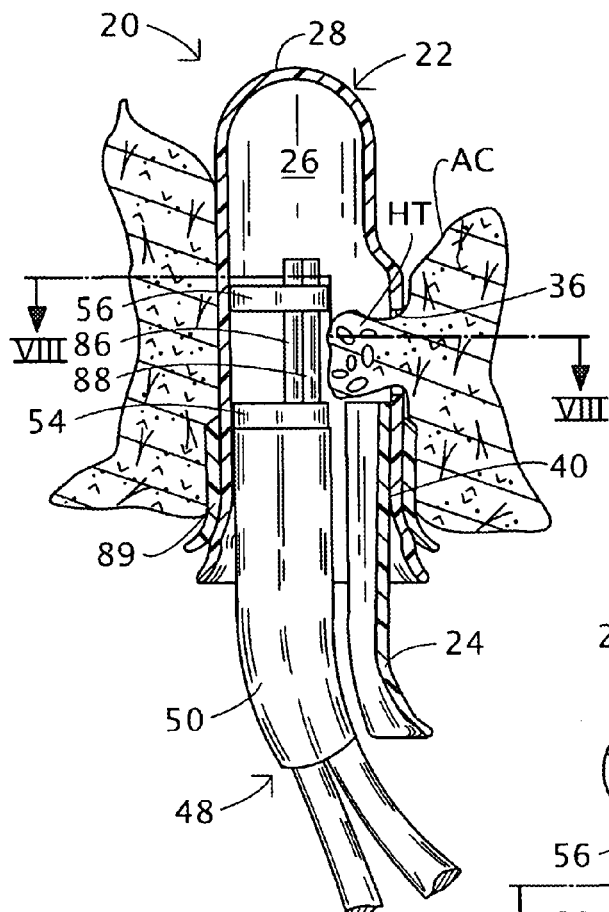
Figure 7D:
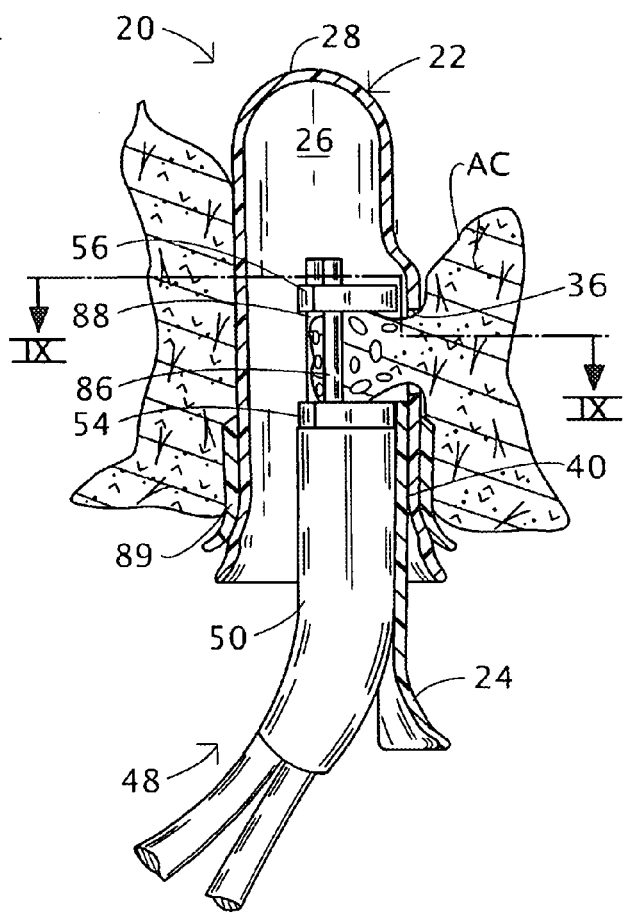

Upon an appropriate positioning of anoscope 20, shutter member 24 is grasped at an external flange or finger grip 90 and pulled in a proximal direction, as indicated by an arrow 92 in FIG. 7B. This action uncovers window 36 and enables hemorrhoidal tissues HT to protrude through the window into channel 26 of anoscope 20. Subsequently, a distal end portion of hemorrhoid treatment device 48 particularly including jaws 54 and 56 is inserted into anoscope 20. As depicted in FIG. 7C, this insertion may be performed with jaw 54 and 56 located in channel 26 on a side of longitudinal axis 38 opposite bulging sidewall portion 40 (see FIGS. 7C and 8), whereby the protruding hemorrhoidal tissues HT pass through a slot or gap 94 defined by jaw 56. In that case, after the placement of hemorrhoid treatment device 48, the device is rotated about a longitudinal axis and possibly translated orthogonally to that axis to align jaws 54 and 56 with a neck or base region 96 of the protruding hemorrhoidal tissues HT as shown in FIGS. 7D and 9.

In an alternative deployment procedure, the distal end portion of hemorrhoid treatment device 48 is inserted into anoscope 20 in such a manner that jaws 54 and 56 are located in channel 26 on the same side of longitudinal axis 38 as bulging sidewall portion 40 (see FIGS. 7C and 8). Because the protruding hemorrhoidal tissues HT are malleable, distal jaw 56 of hemorrhoid treatment device 48 may be slipped past the protruding tissues. It may be necessary or expedient to wiggle hemorrhoid treatment device 48 during the insertion (and removal) phase of a deployment operation, depending on the relative sizes of anoscope 20, hemorrhoid treatment device 48, and the protruding hemorrhoidal tissues HT. In this alterantive deployment procedure, there is no need to rotate device 48 about a longitudinal axis to align jaws 54 and 56 with a neck or base region 96 of the protruding hemorrhoidal tissues HT as shown in FIGS. 7D and 9.

Figure 7E:
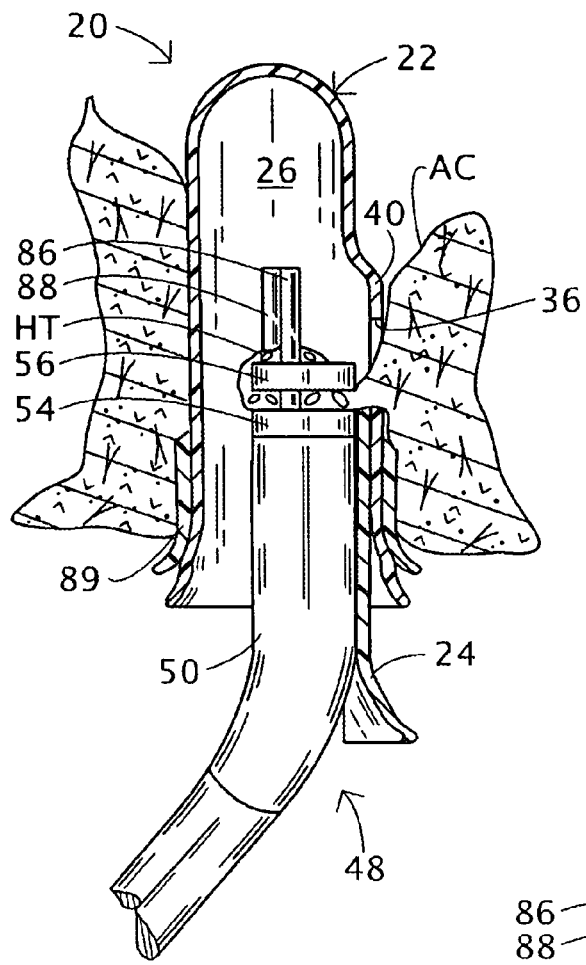

With jaws 54 and 56 located on opposite sides of hemorrhoidal tissues HT, the are approximated, as depicted in FIG. 7E, to clamp the hemorrhoidal tissues HT. Preferably, jaws 54 and 56 are maintained in parallel to one another during their closing and opening strokes.

While jaws 54 and 56 are clamped about neck region 96 of tissues HT as shown in FIG. 7E, the tissue occlusion component (FIGS. 3–6) of the hemorrhoid treatment device 48 is operated to permanently constrict hemorrhoidal tissues HT in or about neck region 96. In the case of stapling mechanism 58 (FIG. 3), staples 60 are fired through ejection apertures 62 in jaw 54 by a distal motion of pusher elements 64, the staples being closed upon meeting respective anvil elements (not illustrated) in distal jaw 56. In the case of injection mechanism 66 (FIG. 4), hollow needles 68 fixed to proximal jaw 54 are naturally or automatically inserted into hemorrhoidal tissues during the approximation of jaws 54 and 56. Sclerosing composition is then guided from reservoir 72 into the hemorrhoidal tissues HT. In the case of radiant-energy applicator 74 (FIG. 5), the applicator is operated to generate electromagnetic radiation of a predetermined spectral range, which is then directed into hemorrhoidal tissues HT via optical fibers 76. In the case of the RF-cautery componentry of FIG. 6, radio-frequency current is conducted from source 84 through electrode 82 into hemorrhoidal tissues HT. Where distal electrode 56 is also provided with an electrode, the current passes from electrode 82 through neck or base region 96 to jaw 56. In the case of a monopolar cauterization current, the current spread out from tissues HT into the patient's body.

Figure 7F:
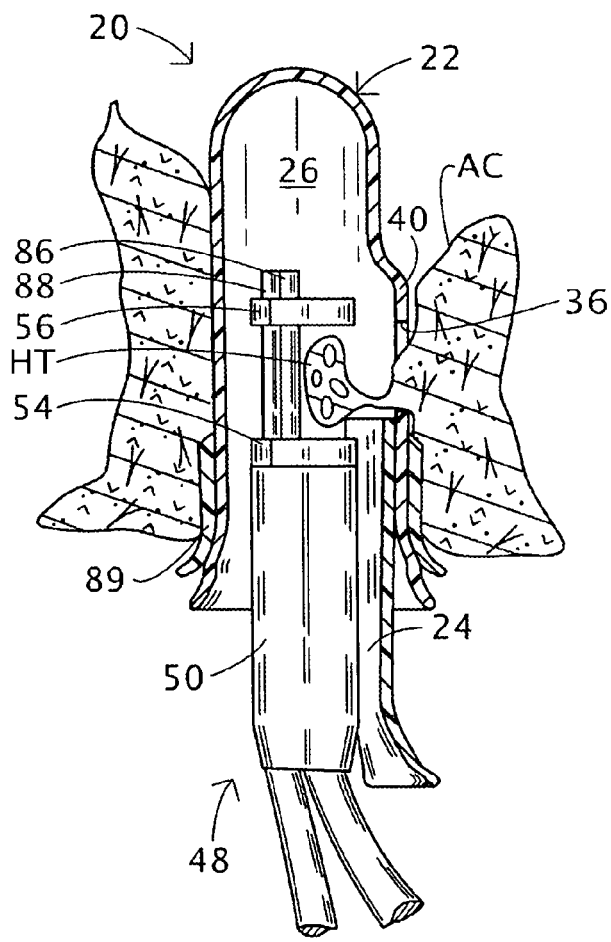

After the occlusion operation has been performed, handle 52 is operated to separate jaws 54 and 56 from one another and the treatment device 48 is manipulated to separate the jaws from the treated hemorrhoidal tissues HT (FIG. 7F). Treatment device 48 is then further manipulated to withdraw it from anoscope 20. Again, because of the deformability of the clamped hemorrhoidal tissues HT, in many cases it will be possible to simply withdraw the hemorrhoid treatment device 48 without rotation, but perhaps with some wiggling.

The hemorrhoidal tissues HT distal to the occluded neck region 96 may be transected with a scalpel or allowed to ischemically regress or self amputate. Self-amputation occurs within a few days of the occlusion procedure. Ischemic regression takes place within several weeks. Ischemic regression and self-amputation are the result of occlusion of bloods vessels in neck or base region 96.

Bulging portion or protrusion 40 of anoscope 20 serves as a retractor of collateral anal or rectal tissues. In addition, bulging portion or protrusion 40 creates more work space in the area of hemorrhoidal tissues HT. This design allows for better access to the neck or base 96 of tissues HT, which is located in the submucosal layer close to the rectal muscle.

FIGS. 8–10 show one configuration of bulging portion or protrusion 40, where the protrusion has a radius of curvature that is greater than a radius of curvature of the remaining part of hollow body 22. Other configurations are possible. FIG. 11 depicts a configuration where a bulging portion or protrusion 98 has a radius of curvature that is smaller than the radius of curvature of the main part of hollow body member 22. FIG. 12 illustrates a configuration where a bulging portion or protrusion 100 has a radius of curvature that is essentially equal to the radius of curvature of the main part of hollow body member 22. The dashed lines 102, 104, 106 represent the respective occluding jaws of hemorrhoid treatment device 48.

Generally, the manipulating of anoscope 20 to align window 36 with hemorrhoidal tissues is performed after the inserting of anoscope 20 into the anal canal. Anoscope 20 and port member 89 are preferably made of a transparent polymeric material that facilitates visual inspection and locating of the hemorrhoids. Jaws 54 and 56 of the occlusion device are inserted into anoscope 20 after the inserting of anoscope 20 into the anal canal AC, after the manipulating of anoscope 20 to align window 36 with hemorrhoidal tissues HT, and after the protruding of the hemorrhoidal tissues HT through window 36.

A hemorrhoid treatment instrument or device as disclosed hereinabove may be partially or completely disposable. Where both jaws 54 and 56 are parts of a disposable cartridge removably attached to shaft 50, the proximal portion of the instrument may be utilizable in treating different patients at different times. Alternatively or additionally, where proximal jaw 54 contains a staple magazine, jaw 54 may be replaceable to permit multiple hemorrhoid occlusion procedures on the same patient.

Although the invention has been described in terms of particular embodiments and applications, one of ordinary skill in the art, in light of this teaching, can generate additional embodiments and modifications without departing from the spirit of or exceeding the scope of the claimed invention. For example, rods 86 and 88 may be fixed to distal jaw 56 and slidably connected to shaft 50. Alternatively, rods 86 and 88 may be fixed to both distal jaw 56 and shaft 50, in which case proximal jaw 54 is slidable along rods 86 and 88 alternately towards and away from jaw 56. Also, more than two rods 86 and 88 may be provided for coupling distal jaw 56 to instrument shaft 50.

In yet another alternative design, both jaws 54 and 56 are movable along rods 86 and 88 during a clamping or closure stroke. Such a design facilitates hemorrhoid occlusion without tearing of the tissues below the occluded tissue base. If only one jaw 54 or 56 is movable along rods 86 and 88, then the entire instrument could be moved relative to the patient during closure of the jaws to ensure against undesired tissue tears. Where the distal jaw 56 is slidable along rods 86 and 88, the entire instrument is pushed into the patient while the distal jaw is moving in a proximal direction.

Accordingly, it is to be understood that the drawings and descriptions herein are proffered by way of example to facilitate comprehension of the invention and should not be construed to limit the scope thereof.

What is claimed is:

1. A method for the treatment of hemorrhoids, comprising:
providing an anoscope and a hemorrhoid occlusion device, said anoscope including a hollow body having a sidewall provided with a window, said hemorrhoid occlusion device having a distal end provided with a pair of jaws, at least a distal one of said jaws including a clamping member;
inserting said anoscope into an anal canal;
manipulating said anoscope so that hemorrhoidal tissues protrude through said window into said anoscope;
inserting said jaws of said occlusion device into said anoscope;
after the protruding of said hemorrhoidal tissues through said window and after the inserting of said jaws into said anoscope, manipulating said occlusion device so that said jaws are located on opposite sides of the hemorrhoidal tissues, the manipulating of said occlusion device including manipulating said occlusion device so that one of said jaws is located on a far or distal side of the hemorrhoidal issues, between the hemorroidal tissues and an inner or distal end of said anoscope, and so that another of said jaws is located on a near or proximal side of the hemorrhoidal tissues, between the hemorroidal tissues and an outer or proximal end of said anoscope;
thereafter closing said jaws to clamp the hemorrhoidal tissues; and
subsequently operating a tissue occlusion component of said occlusion device to permanently constrict a portion of said hemorrhoidal tissues.

2. The method defined in claim 1 wherein the manipulating of said anoscope including turning said anoscope about a longitudinal axis so that said hemorrhoidal tissues are aligned with said window.

3. The method defined in claim 2 wherein the turning of said anoscope is carried out after the inserting of said anoscope into the anal canal.

4. The method defined in claim 1 wherein the jaws of said occlusion device are inserted into said anoscope after the inserting of said anoscope into the anal canal.

5. The method defined in claim 4 wherein the jaws of said occlusion device are inserted into said anoscope after the protruding of the hemorrhoidal tissues through said window.

6. The method defined in claim 1 wherein said anoscope includes a shutter member for covering said window, wherein the inserting of said anoscope into the anal canal includes inserting said anoscope with said shutter member covering said window, further comprising moving said shutter member to uncover said window to permit said hemorrhoidal tissues to protrude through said window.

7. The method defined in claim 6 wherein the moving of said shutter member including sliding said shutter member relative to said anoscope.

8. The method defined in claim 7 wherein said anoscope has a longitudinal axis, said sidewall being formed with a bulging portion located on one side of said axis and extending from a proximal end of said anoscope partially along a length of said sidewall towards a distal end of said anoscope, said window being located in said bulging portion, said shutter member being slid along and in engagement with said bulging portion.

9. The method defined in claim 1, further comprising maintaining said jaws in parallel to one another during the closing of said jaws.

10. The method defined in claim 1 wherein the operating of said tissue occlusion component includes an action taken from the group consisting of stapling the hemorrhoidal tissues, injecting the hemorrhoidal tissues with a sclerosing composition, and irradiating the hemorrhoidal tissues with laser radiation.

11. The method defined in claim 1 wherein the closing of said jaws includes linearly translating at least one of said jaws towards the other of said jaws.

12. The surgical instrument assembly defined in claim 1 wherein said jaws define a U-shaped occlusion area.

13. A surgical instrument assembly for the treatment of hemorrhoids, comprising an anoscope and a hemorrhoid occlusion device,
said anoscope including a hollow body defining a longitudinal channel, said hollow body being closed at a distal end and at least partially open at a proximal end, said hollow body having a sidewall provided with a window spaced from at least said distal end,
said hemorrhoid occlusion device including an instrument shaft provided at a distal end with two jaws, at least one of said jaws including a clamping member movable alternately away and towards the other of said jaws for clamping and occluding hemorrhoidal tissues protruding through said window into said anoscope, said jaws being insertable into said anoscope so that said jaws are located on opposite side of hemorrhoidal tissues protruding through said window into said anoscope, said jaws being mounted to a pair of parallel rods each connected at one end to said shaft.

14. The surgical instrument assembly defined in claim 13 wherein said jaws extend in planes oriented substantially perpendicularly to said rods.

15. The surgical instrument assembly defined in claim 13 wherein a given one of said jaws is slidably coupled to said rods, the other of said jaws being fixed with respect to said rods.

16. The surgical instrument assembly defined in claim 13 wherein said rods are coupled to opposite sides of each of said jaws.

17. The surgical instrument assembly defined in claim 13 wherein said hemorrhoid occlusion device further includes a hemorrhoid occlusion component mounted to said jaws for acting on tissues gripped between said jaws, to couple said tissues to each other.

18. The surgical instrument assembly defined in claim 17 wherein said hemorrhoid occlusion component is taken from the group consisting of a stapling mechanism, an injection mechanism connectable to a reservoir of a sclerosing composition, and radiation guide elements connectable to a source of electromagnetic radiation.

19. The surgical instrument assembly defined in claim 18 wherein said occlusion component is a stapling mechanism including a staple cartridge removably mounted to one of said jaws.

20. The surgical instrument assembly dt fined in claim 13 wherein said anoscope further includes a shutter member mounted to said hollow body to cover said window during a positioning of the anoscope in an anal canal, said shutter member being movable relative to said hollow body to uncover said window to permit hemorrhoidal tissues to protrude through said window into said channel.

21. The surgical instrument assembly dt fined in claim 13 wherein said hollow body has a longitudinal axis, said sidewall being formed with a bulging portion located on one side of said axis and extending from said proximal end partially along a length of said sidewall towards said distal end, said window being located in said bulging portion.

22. The surgical instrument assembly defined in claim 13 wherein said jaws are mounted to said shaft so as to remain parallel to one another during opening and closing strokes of said jaws.

23. The surgical instrument assembly defined in claim 13 wherein said one of said jaws is located proximally of said other of said jaws.

24. The surgical instrument assembly defined in claim 13 wherein said jaws are parts of a cartridge removably attachable to said shaft.

25. The surgical instrument assembly defined in claim 13 wherein said occlusion device includes a removable cartridge member incorporated in at least one of said jaws.

26. The surgical instrument assembly defined in claim 13 wherein said jaws define a U-shaped occlusion area.

27. A surgical instrument assembly for the treatment of hemorrhoids, comprising an anoscope, a closure member, and a hemorrhoid occlusion device, said anoscope including a hollow body having a longitudinal axis and defining a longitudinal channel, said hollow body being closed at a distal end and at least partially open at a proximal end, said hollow body having a sidewall formed with a bulging portion located on one side of said axis and extending from said proximal end partially along a length of said sidewall towards said distal end, said bulging portion being provided with a window spaced from at least said distal end, said closure member being slidably connectable to said hollow body in said bulging portion for alternately covering and uncovering said window, said hemorrhoid occlusion device including an instrument shaft provided at a distal end with two jaws, at least one of said jaws including a clamping member movable alternately away and towards the other of said jaws for clamping and occluding hemorrhoidal tissues protruding through said window into said anoscope, said jaws being insertable into said anoscope so that said jaws are located on opposite side of hemorrhoidal tissues protruding through said window into said anoscope.

28. The surgical instrument assembly defined in claim 27 wherein said hemorrhoid occlusion device further includes a hemorrhoid occlusion component mounted to said jaws for acting on tissues gripped between said jaws, to couple said tissues to each other.

29. The surgical instrument assembly defined in claim 28 wherein said hemorrhoid occlusion component is taken from the group consisting of a stapling mechanism, an injection mechanism connectable to a reservoir of a sclerosing composition, and radiation guide elements connectable to a source of electromagnetic radiation.

30. A surgical instrument assembly for the treatment of hemorrhoids, comprising an anoscope and a hemorrhoid occlusion device, said anoscope including a hollow body defining a longitudinal channel, said hollow body being closed at a distal end and at least partially open at a proximal end, said hollow body having a sidewall provided with a window spaced from at least said distal end, said hemorrhoid occlusion device including an instrument shaft provided at a distal end with two jaws, at least one of said jaws including a clamping member movable alternately away and towards the other of said jaws for clamping and occluding hemorrhoidal tissues protruding through said window into said anoscope, said jaws being insertable into said anoscope so that said jaws are located on opposite side of hemorrhoidal tissues protruding through said window into said anoscope, wherein said jaws are insertable into said anoscope so that one of said jaws is located on a far or distal side of hemorrhoidal tissues protruding through said window into said anoscope, between the protruding hemorroidal tissues and an inner or distal end of said anoscope, and so that another of said jaws is located on a near or proximal side of the protruding hemorrhoidal tissues, between the protruding hemorroidal tissues and an outer or proximal end of said anoscope.

31. The surgical instrument assembly defined in claim 30 wherein said jaws are mounted for linear translation alternately towards and away from one another.

* * * * *